United States Patent
Lowenstein et al.

(10) Patent No.: US 8,550,078 B2
(45) Date of Patent: Oct. 8, 2013

(54) INFLATION AND MONITORING ASSEMBLY FOR A PRESSURE CUFF OF AN ENDOTRACHEAL TUBE

(75) Inventors: Stephen Jay Lowenstein, Englewood Cliffs, NJ (US); Michael R. Cole, Stratham, NH (US); Klaus D. Lessnau, New York, NY (US); Keith Rubin, Fort Lauderdale, FL (US); James M. Sellers, Portsmouth, NH (US)

(73) Assignee: Seedlings Life Science Ventures, LLC., New York, NY (US)

( * ) Notice: Subject to any disclaimer, the term of this patent is extended or adjusted under 35 U.S.C. 154(b) by 683 days.

(21) Appl. No.: 12/661,103

(22) Filed: Mar. 10, 2010

(65) Prior Publication Data
US 2011/0220118 A1    Sep. 15, 2011

(51) Int. Cl.
| | | |
|---|---|---|
| *A62B 7/00* | (2006.01) | |
| *A62B 9/00* | (2006.01) | |
| *A61M 16/00* | (2006.01) | |
| *G01L 7/00* | (2006.01) | |

(52) U.S. Cl.
USPC .................. 128/205.23; 128/207.15; 73/700

(58) Field of Classification Search
USPC ............ 128/200.26, 205.23, 207.14, 207.15; 604/96.01, 97.01–3, 100.01–3, 110, 604/121, 240–243, 533–536, 920; 606/192, 606/196; 600/560, 561, 593; 73/700, 73/714–716, 729.1, 729.2; 417/63, 559
See application file for complete search history.

(56) References Cited

U.S. PATENT DOCUMENTS

| | | | |
|---|---|---|---|
| 3,941,149 A * | 3/1976 | Mittleman ................. 137/493.1 |
| 4,016,885 A | 4/1977 | Bruner | |
| 4,159,722 A * | 7/1979 | Walker .......................... 137/496 |
| 4,361,107 A | 11/1982 | Gereg | |
| 4,501,273 A | 2/1985 | McGinnis | |
| 4,526,196 A | 7/1985 | Pistillo | |
| 4,617,015 A | 10/1986 | Foltz | |
| 5,218,970 A | 6/1993 | Turnbull et al. | |
| 5,235,973 A | 8/1993 | Levinson | |
| 5,336,183 A | 8/1994 | Greelis et al. | |
| 5,421,325 A | 6/1995 | Cinberg et al. | |
| 5,487,383 A | 1/1996 | Levinson | |
| 5,492,536 A | 2/1996 | Mascia | |
| 5,518,376 A * | 5/1996 | Haraoka ........................ 417/437 |
| 5,591,130 A | 1/1997 | Denton | |
| 5,637,101 A * | 6/1997 | Shillington .................... 604/242 |

(Continued)

FOREIGN PATENT DOCUMENTS

WO    WO 2011/112231    9/2011

*Primary Examiner* — Jackie Ho
*Assistant Examiner* — Mark K Han
(74) *Attorney, Agent, or Firm* — Malloy & Malloy, P.L.

(57) ABSTRACT

An assembly structured to inflate a retaining or pressure cuff associated with an artificial airway tube such as an endotracheal and/or tracheotomy tube and concurrently monitor pressure therein including a casing having an interior pressure chamber. A pump assembly is movably connected to the casing and structured to force fluid flow to the retaining cuff through said pressure chamber. An indicator member is disposed within the casing, is visually accessible through casing window, and is variably positionable dependent on and indicative of existing pressure within the retaining cuff. The existing pressure within the pressure chamber is substantially equivalent to that within the retaining cuff thereby facilitating the variable position of the indicator member to indicate pressure within the cuff. A junction is disposed between the casing and an inflation lumen to the restraining cuff and is structured to allow disconnection between the casing and the lumen but prevent reconnection thereto.

15 Claims, 17 Drawing Sheets

(56) References Cited

U.S. PATENT DOCUMENTS

| | | | |
|---|---|---|---|
| 5,902,273 A | 5/1999 | Yang et al. | |
| 5,992,239 A * | 11/1999 | Boehringer et al. | 73/715 |
| 6,267,749 B1 | 7/2001 | Miklos et al. | |
| 6,530,898 B1 | 3/2003 | Nimkar et al. | |
| 6,553,993 B2 | 4/2003 | Toti et al. | |
| 6,705,320 B1 | 3/2004 | Anderson | |
| 6,979,316 B1 | 12/2005 | Rubin et al. | |
| 7,018,359 B2 | 3/2006 | Igarashi et al. | |
| 7,383,736 B2 | 6/2008 | Esnouf | |
| 7,404,329 B2 | 7/2008 | Quinn et al. | |
| 8,033,176 B2 | 10/2011 | Esnouf | |
| 2006/0150742 A1* | 7/2006 | Esnouf | 73/716 |
| 2008/0200871 A1* | 8/2008 | Slater et al. | 604/96.01 |
| 2010/0179488 A1 | 7/2010 | Spiegel et al. | |
| 2011/0220116 A1 | 9/2011 | Lowenstein et al. | |
| 2011/0220119 A1 | 9/2011 | Lowenstein et al. | |
| 2012/0255555 A1 | 10/2012 | Lowenstein et al. | |

* cited by examiner

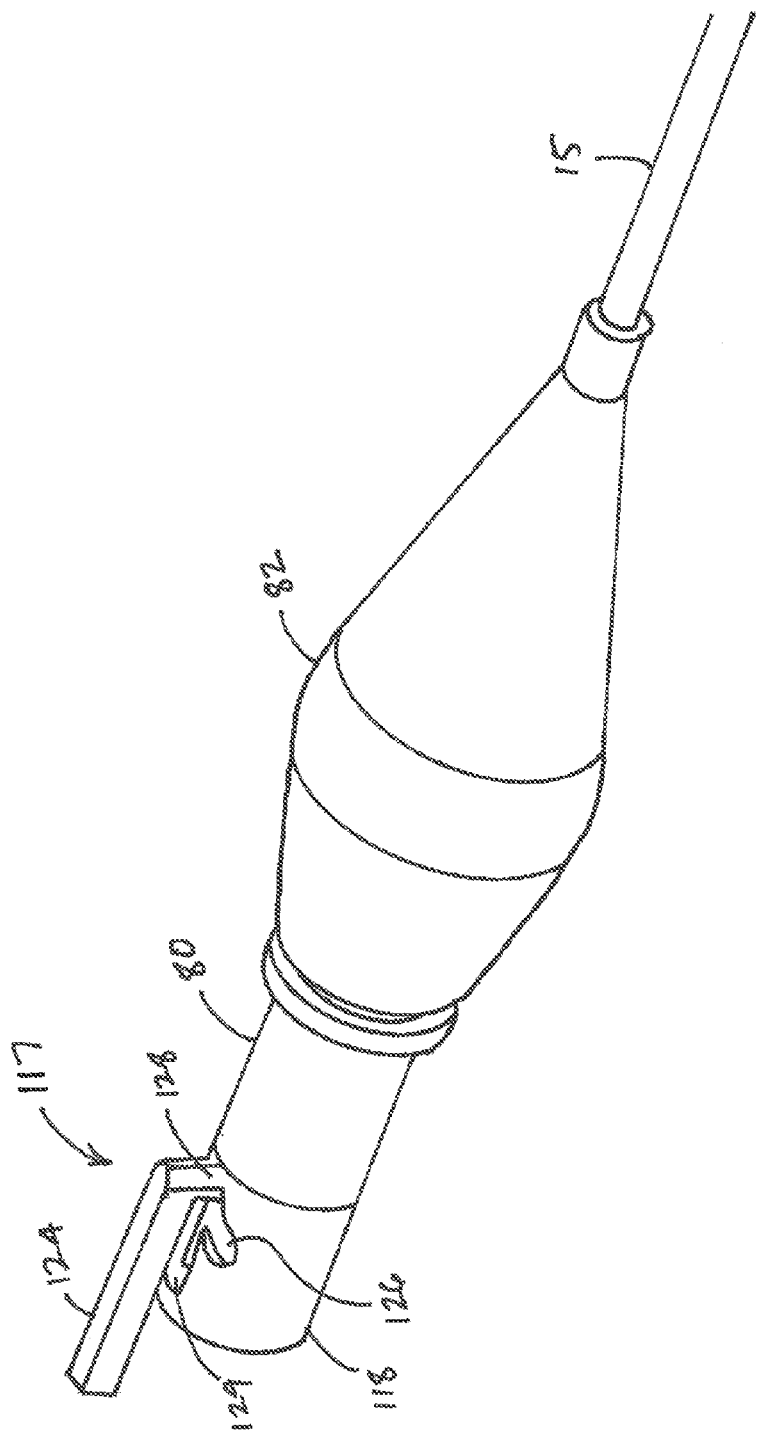

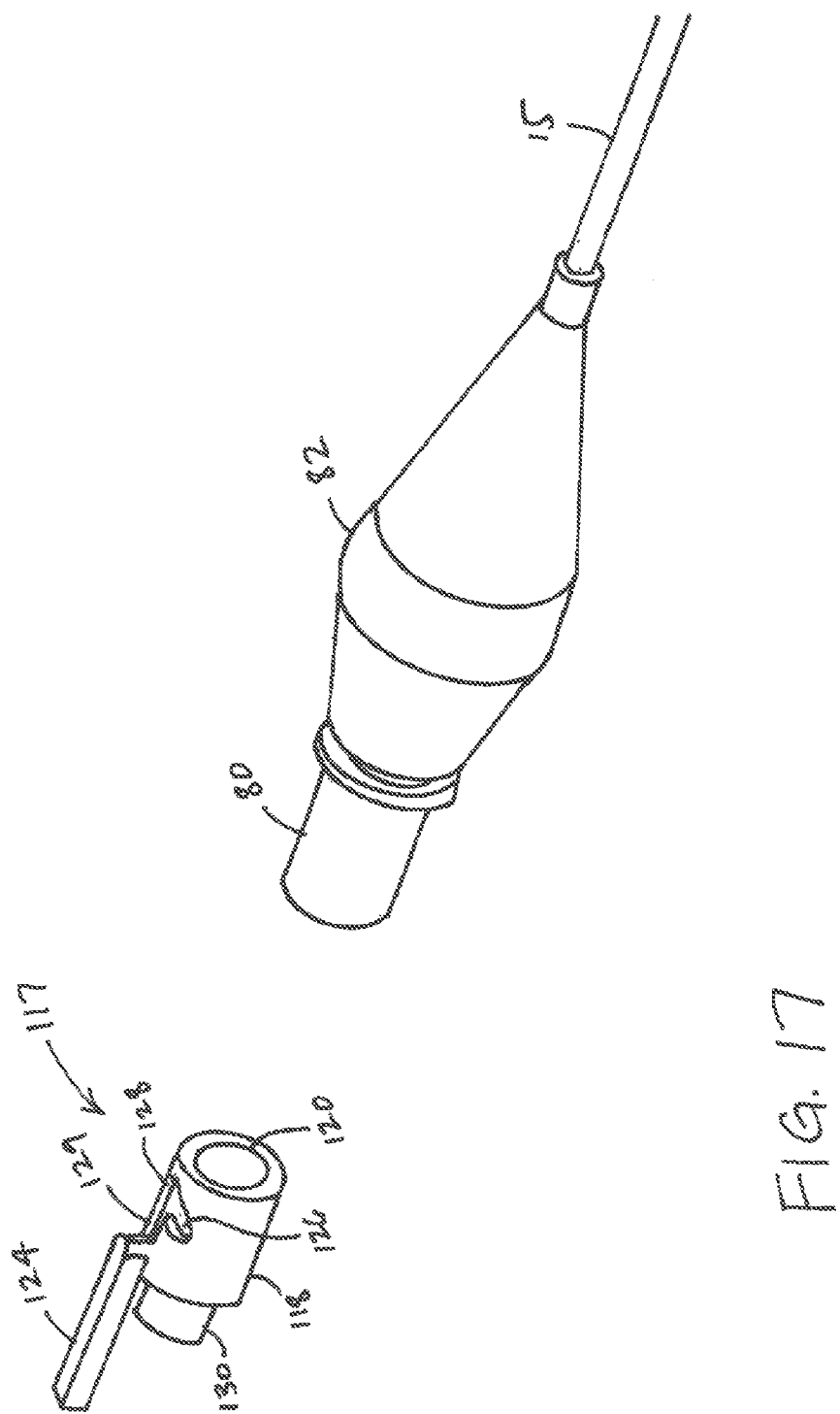

INFLATION AND MONITORING ASSEMBLY FOR A PRESSURE CUFF OF AN ENDOTRACHEAL TUBE

BACKGROUND OF THE INVENTION

1. Field of the Invention

This invention is directed to an assembly structured to inflate and continuously monitor pressure within a retaining cuff associated with an endotracheal tube and/or tracheostomy tube including a casing having a pump assembly operative to inflate the retaining cuff. An indicator assembly is readily observable and variably positioned on the casing in response to the existing pressure of the cuff. An interconnecting junction secures the casing to an inflating lumen communicating with the cuff and in at least one embodiment is structured to permit disconnection of the casing from the lumen but prevent reconnection therebetween.

2. Description of the Related Art

The use of endotracheal tubes is well known in the medical profession. In practice, the tube is inserted through the mouth of the patient into the trachea and is structured, when properly positioned, to facilitate ventilation from a ventilator or the like.

As conventionally used, the endotracheal tube and/or tracheostomy tube includes a coupling structure at the proximal or outer end thereof which connects the lumen of the endotracheal and/or tracheostomy tube to the source of ventilation. The endotracheal and/or tracheostomy tube commonly includes an inflatable, pressure or retaining cuff which is generally disposed in surrounding relation to the distal end of the tube. In use, the cuff is inflated and thereby serves to secure or stabilize the position of the tube as it expands radially outward into confronting relation to the walls of the trachea. As a result, the inflated cuff serves to stabilize the position of the endotracheal tube and also establishes a seal within the trachea. As conventionally structured, a conduit is associated with the tube and includes an interior, inflating lumen used to inflate the cuff when the endotracheal tube is properly positioned within the trachea. Dependent on the structure and use of the endotracheal tube, the inflating line or conduit may be integrally formed on or within the primary wall of the tube itself. As such, the cuff is manually inflated by an appropriate inflation assembly such as, but not limited to, a separate, removable syringe connected in fluid communication with the inflating lumen. Moreover, the cuff is inflated to a pressure which accomplishes the above noted seal with the interior of the trachea, as well as effect the aforementioned stabilization of the endotracheal and/or tracheostomy tube.

The importance of under inflation, over inflation and/or excessive pressurization of the retaining cuff is well recognized, due to the potential of resulting injury and/or trauma to the patient. Accordingly, when the pressure within the cuff is too low, the sealing function thereof cannot be fully achieved resulting in possible leakage of saliva, air, etc. into the trachea. However, an over pressurization of the cuff may result in reduced blood flow to tracheal tissue, tracheal ischemic conditions, and cause ulcers, bleeding and tracheal stenosis or tracheomalacia after removal of the tube, which can lead to the need for tracheal repair surgery or even a tracheal transplant. Accordingly, it is important to maintain the inner pressure of the cuff, depended on its structure and design, within predetermined ranges in order to affect both the above noted fluid seal with the trachea as well as stabilization of the endotracheal tube within the trachea.

Known attempts to overcome problems of the type set forth above have resulted in the provision of various types of pressure gauges or other pressure monitoring devices connected in fluid communication with the inflating lumen and with the pressure or retaining cuff itself. However, many of these known or conventional attempts to accurately monitor cuff pressure have resulted in less than accurate or satisfactory results. Accordingly, while known monitoring devices may be at least minimally effective for their intended function, they have been found to be relatively bulky, cumbersome, costly, and/or less than efficient. Indeed, because of these factors, monitoring devices are often not available at the bed side and ET cuff pressure monitoring is often inadequately addressed, both initially as well as after the patient is intubated. Moreover, even if a one time, initial pressure identification is achieved, such is inadequate because the pressure can change over time, such as when the patient is moved or the endotracheal tube is re-positioned, or when ventilation settings are adjusted. As a result, there is a need in the medical profession for an assembly structured to properly inflate and continuously monitor the pressure within a retaining or pressure cuff of an endotracheal and/or tracheostomy tube. Further, the inflating and monitoring functions of a proposed monitoring assembly should preferably be carried out by a single unit which may be incorporated within the endotracheal tube assembly or alternatively may be connected thereto. As such, the monitoring of the pressure within the retaining cuff should be effectively accomplished by a mere visual observation of the preferred assembly, without requiring repeated attachment and removal of a pressure monitor and/or inflating device. In addition, such a preferred monitoring and inflating assembly should be easily operable, and in certain preferred embodiments may be structured to be used as a single use device, which is not integrated into the endotracheal tube, but readily connectable to an inflation lumen of the tube and subsequently detachable there from, but further wherein reconnection of the monitoring assembly is prevented so that re-use of the device is prevented to avoid cross-contamination of infection from patient to patient.

SUMMARY OF THE INVENTION

The present invention is directed to an assembly structured to inflate and monitor the pressure within a retaining or pressure cuff of the type associated with an artificial airway tube such as, but not limited to, an endotracheal and/or a tracheostomy tube. In typical fashion, the retaining or pressure cuff is connected to or associated with the distal end of the endotracheal tube and is radially expanded, such as by inflation and pressurization. When inflated the cuff serves to retain the associated tube in an intended position within the trachea of a patient and form a seal therewith. It is emphasized that while the structural and operative features of the assembly of the present invention are applicable for use with a retaining/pressure cuff, associated with the aforementioned artificial airway tube(s), it is not intended to be limited to such use. More specifically, the inflation and monitoring assembly of the present invention can be used to perform the intended and described functions when operatively associated with retaining or pressure cuffs used for a plurality of other purposes.

Accordingly, the assembly of the present invention is structured to efficiently inflate the retaining or pressure cuff so as to orient it in a retaining, sealing position within the trachea. During and subsequent to inflation, the assembly of the present invention is structured to monitor the existing pressure within the cuff in order to avoid over inflation and/or over pressurization thereof. More specifically, the assembly of the present invention comprises a casing which is connected to the inflating lumen of the endotracheal tube, leading to the retaining cuff, by means of a connection assembly. In at least one preferred embodiment of the present invention, the connection assembly is structured to selectively assume a connect orientation or a disconnect orientation. When in the connect orientation the connection assembly is disposed or oriented to connect to the inflating lumen and establish and maintain fluid flow between the casing of the assembly and the interior of the retaining cuff. However, when in the disconnect orientation, the connection assembly is structured to allow disconnection and removal of the casing from the inflation lumen and further structured to prevent reconnection therebetween. Therefore, at least one preferred embodiment of the present invention comprises a single-use inflation and monitoring assembly. As a result, once the casing of the assembly is disconnected from the inflating lumen, it is not reusable at least to the extent of being reconnected to the inflating lumen. However, structural modifications of the connection assembly may be included in an additional preferred embodiment, wherein the inflation and monitoring assembly of the present invention may be fixedly and/or permanently connected to the inflation lumen and be used therewith as an integrated unit.

Additional structural and operative features associated with the inflation and monitoring assembly of the present invention include the existence of a pressure chamber on the interior of the casing. In addition, a pump assembly, preferably in the form of a plunger movably connected to the casing between and outwardly extended position and an inwardly directed, compressed position. Therefore, the pump assembly of the present invention is structured for selective manipulation to direct fluid flow from an exterior of the casing into the pressure chamber and therefrom through a remainder of the casing and into the inflating lumen attached to the casing. A valve assembly is operatively disposed in flow regulating relation between the pump assembly and the interior of the pressure chamber. The valve assembly includes a first valve structure serving to regulate fluid flow from an exterior of the casing into the interior of the pump plunger, as the plunger is drawn or forced into the outwardly extended position. In contrast, the second valve structure of the valve assembly is structured to regulate fluid flow from the interior of the plunger into the interior of the pressure chamber. The inward movement of the plunger into a compressed position forces air or fluid flow through the pressure chamber and predetermined remaining portions of the casing, through the connection assembly and into the inflating lumen, where the forced fluid flow travels to the retaining cuff. The cuff is thereby inflated and pressurized. While a preferred embodiment of the present invention comprises the pump assembly structured as an integrated and/or permanent part of the casing, it is noted that the a removable pump assembly, having similar operative and structural characteristics as the plunger, etc., can be removably connected to the casing without departing from the spirit and scope of the present invention.

The assembly of the present invention further includes an indicator assembly comprising an indicator member movably connected to and variably positioned within the casing. The indicator assembly is disposed in direct fluid communication with the interior of the pressure chamber and as a result the position of the indicator member is directly influenced by the existing pressure within the pressure chamber. Moreover, due to the establishment of fluid communication between the interior of the pressure chamber and the interior of the retaining cuff, the existing pressure in the pressure chamber and the retaining cuff will be substantially equivalent. As a result of the existing pressure within the pressure chamber being exerted on the indicator member, the indicator member is "variably positioned" within the casing, dependent on the magnitude of the existing pressure within the pressure chamber, which as set forth above, is the equivalent of the pressure within the cuff.

More specifically, the indicator member can be accurately described as being "variably positioned" within the casing dependent on and indicative of the existing pressure within the pressure chamber. Due to the fact that the existing pressure within the pressure chamber is equivalent to the pressure within the retaining cuff, the variable positioning of the indicator member will be dependent on and indicative of the existing pressure in both the pressure chamber and the retaining cuff.

Other operative and structural features include a window disposed on the casing to facilitate the visual observation of at least a portion of the indicator member. As a result, personnel may easily and efficiently monitor the pressure within the cuff by visually determining the position of the indicator member within the casing. Moreover, the portion of the indicator member viewable through the window may include informative alpha/numeric indicia, color coding, etc. which provides the observer with a clear and easily determinable visual indication as to an acceptable or non-acceptable pressure level within the retaining cuff. In addition, in order to further facilitate the visual observation of the pressure reading, the window may incorporate a magnifying lens or similar structure to make viewing easier. Yet additional embodiments of the present invention may include an LED or other appropriate digital readout, as well as an audible and/or visual warning in the event of an over inflation condition of the cuff.

Additional structural and operative features of the inflation and monitoring assembly of the present invention include a pressure relief assembly. The pressure relief assembly includes at least one relief valve mounted on the casing in an exteriorly accessible location. Further, the pressure relief valve is disposed in direct fluid communication with the interior of the pressure chamber and is disposed in regulating relation to fluid flow vented from the pressure chamber to an exterior of the casing. As a result, the selective manipulation of the relief valve will cause a "bleeding" or venting of air or fluid from within the pressure chamber to the exterior of the casing. As a result the pressure within both the pressure chamber and the retaining cuff may be reduced when it is determined that such pressure is excessive. In addition, the structuring of the relief valve may be tapered or otherwise appropriately structured to provide for a gradual bleeding or release of pressure from within the pressure chamber.

In order to avoid inadvertent venting or release of the pressure within the pressure chamber and retaining cuff, a restricting assembly is selectively positionable on the casing, so as to restrict inadvertent access to the pressure relief valve. The restricting assembly may also be structured to removably lock or otherwise restrictively engage the plunger of the pump assembly thereby preventing its movement and intended operation.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 16 is a perspective view of the embodiment of FIG. 15 wherein the connection assembly has established a connection with an inflating lumen.

FIG. 17 is a perspective view in partial cutaway and exploded form of the embodiment of FIGS. 15 and 16, wherein the connection assembly is disconnected from the inflating lumen, once having been connected thereto.

Like reference numerals refer to like parts throughout the several views of the drawings.

DETAILED DESCRIPTION OF THE PREFERRED EMBODIMENT

Figure 1:
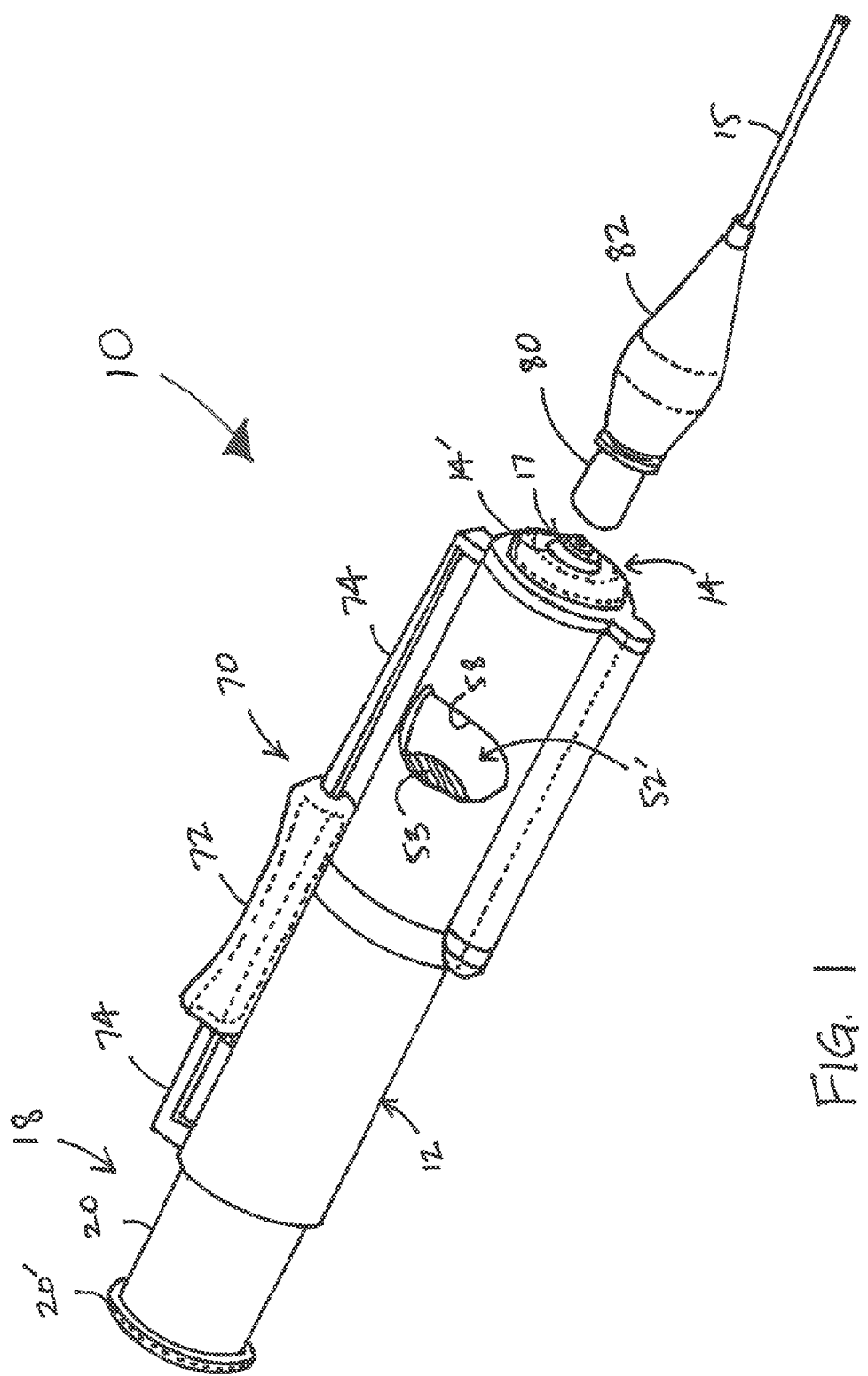
FIG. 1 is a perspective view of the inflating and pressure monitoring assembly of the present invention in an assembled form separated from but connectable to an inflating lumen for an endotracheal tube.

As shown in the accompanying drawings, the present invention is directed to an inflation and pressure monitoring assembly generally indicated as 10. The assembly 10 structured to inflate and monitor the pressure within a retaining cuff or pressure cuff of the type associated with an endotracheal tube.

More specifically, the assembly 10 includes a generally elongated casing 12 having a distal end generally indicated as 14 structured to be interconnected to an inflation lumen 15, which will be described in greater detail hereinafter, by means of a connection assembly 17. The connection assembly 17 is accessible through a receiving port 14' associated with the distal end 14 of the casing 12, and will be described hereinafter with primary reference to FIGS. 12 through 17. As such, the assembly 10 is intended to be interconnected in fluid communication with the inflating lumen 15 and in turn is thereby disposed in direct fluid communication with the interior of the retaining or pressure cuff associated with the inner or distal end of the endotracheal tube and not shown for purposes of clarity.

Figure 2:
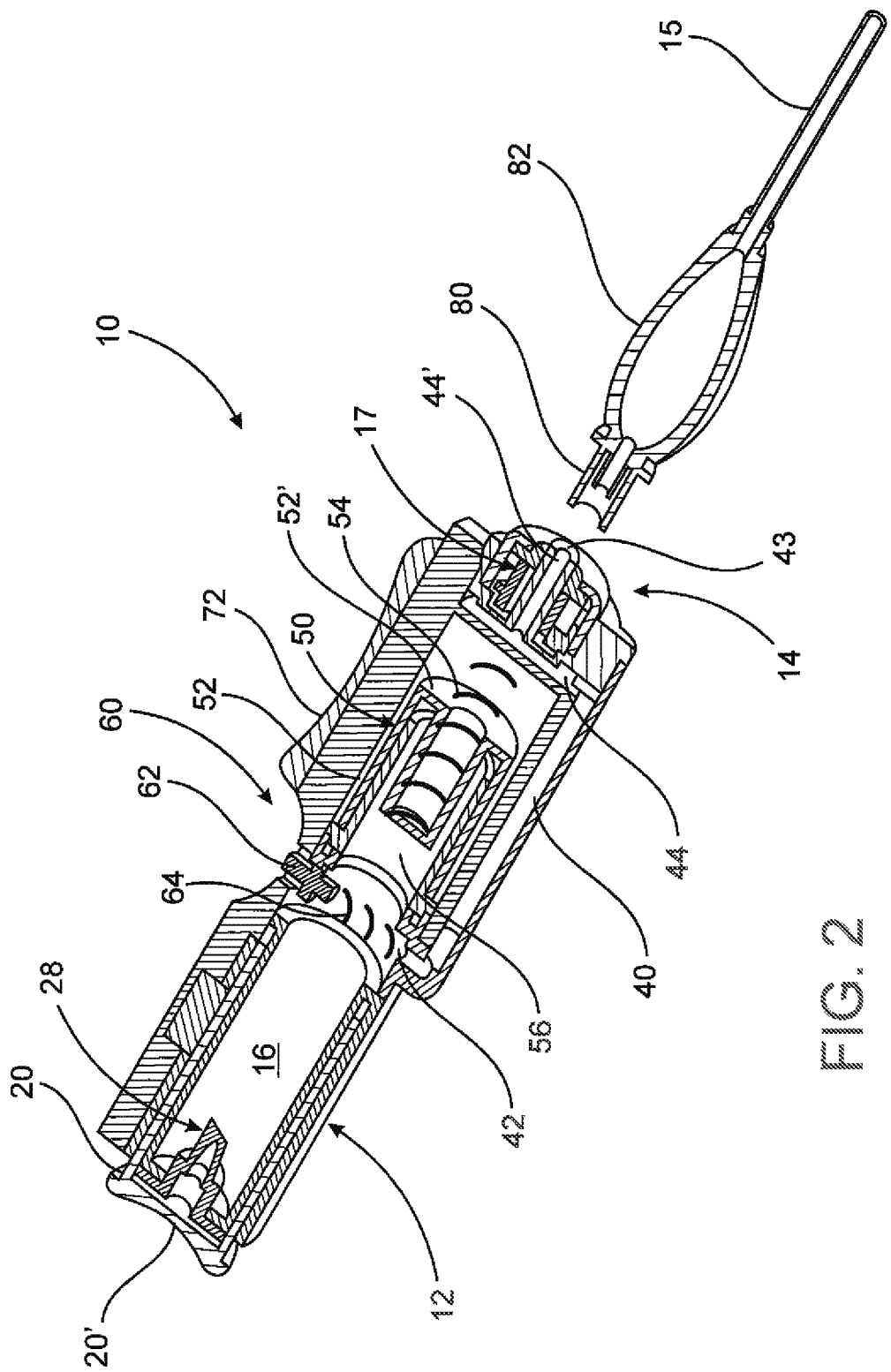
FIG. 2 is a perspective view in longitudinal section of the embodiment of FIG. 1 represented in a different operative orientation.
Figure 3:
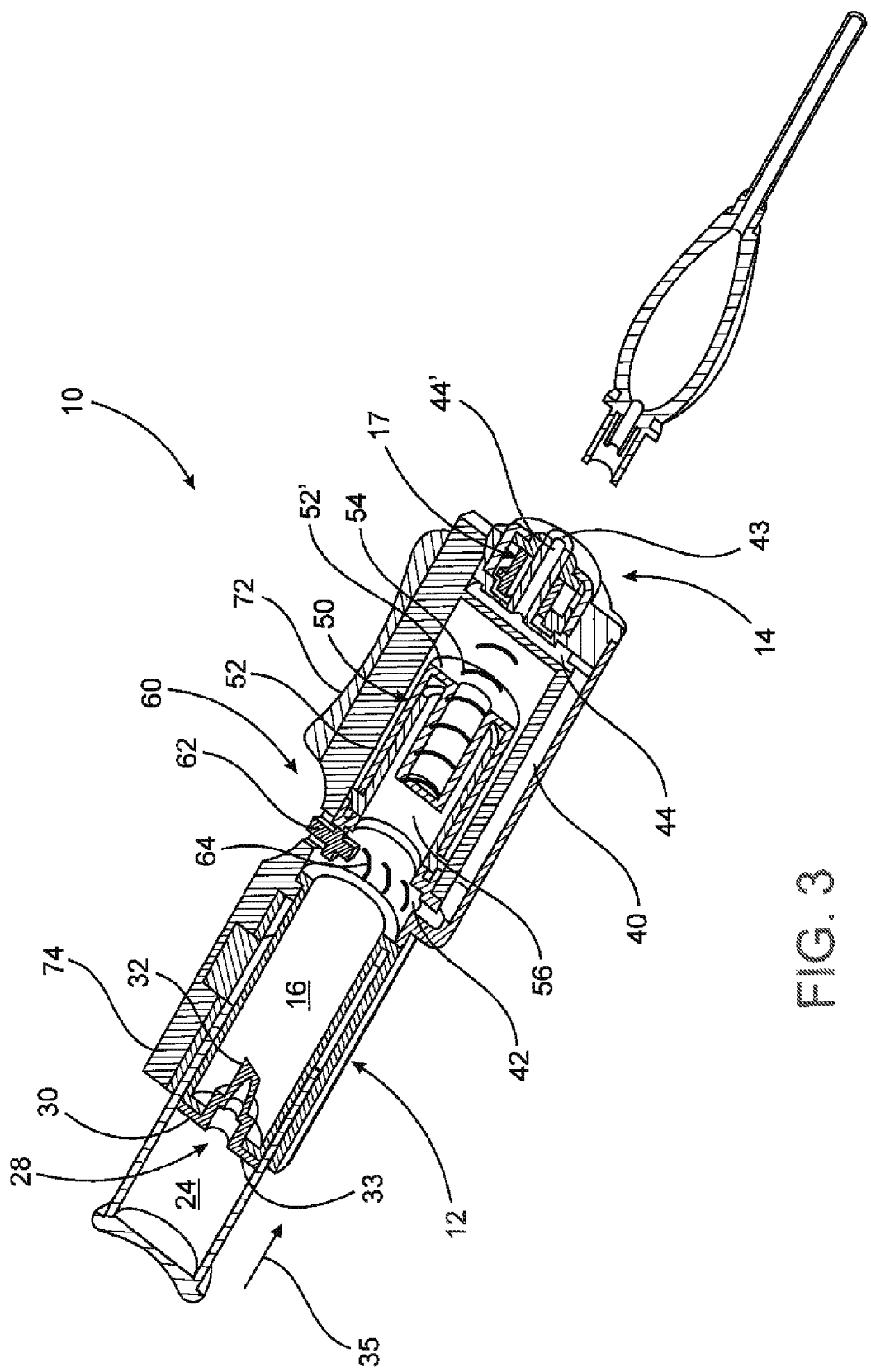
FIG. 3 is a longitudinal sectional view of the embodiment of FIGS. 1 and 2 in the operative orientation of FIG. 1.
Figure 4:
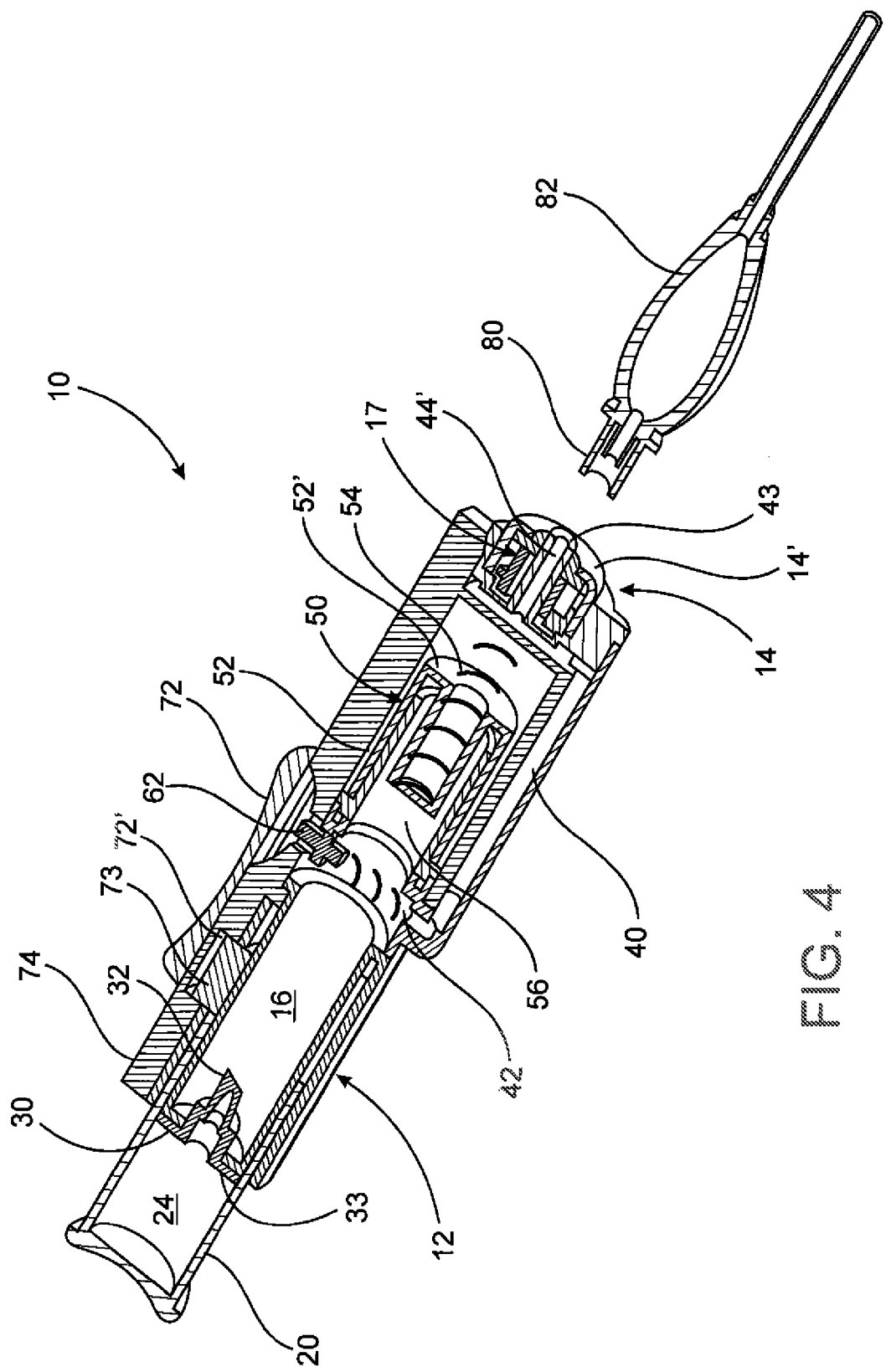
FIG. 4 is a longitudinal sectional view of the embodiment of FIGS. 1-3 in yet a different stage of operation.

With primary reference to FIGS. 1-4, the casing 12 includes an at least partially hollow interior more specifically defined by a pressure chamber 16. A pump assembly generally indicated as 18 is preferably in the form of a plunger 20 having an outer end 20' and an elongated stem or barrel portion. The pump assembly 18 and specifically including the plunger 20 includes a hollow interior 24 extending along substantially the entire length or at least a majority of the plunger 20. The plunger 20 is movably connected to the casing 12 and is selectively disposed between an inwardly directed compressed position as represented in FIG. 2 and an outwardly directed, extended position as represented in FIGS. 1, 3 and 4. Moreover, manipulation of the plunger 20 of the pump assembly 18 will force fluid flow from an exterior of the casing 12 into the pressure chamber 16 and through predetermined portions of the casing 12 to the inflation lumen 15, thereby serving to inflate and pressurize the retainer cuff.

In order to regulate fluid flow to the retainer cuff and maintain a predetermined, acceptable pressure level therein, a valve assembly 28 is associated with the pump 18 and specifically the plunger 20. The valve assembly 28 is disposed in fluid regulating, interconnecting relation between the pressure chamber 16 and the interior 24 of the plunger 20. As such, the valve assembly 28 is disposed and structured to regulate fluid flow from an exterior of the casing 12 into the interior 24 of the plunger 20 and therefrom into the pressure chamber 16. More specifically, the valve assembly 28 includes a first valve structure 30 and a second valve structure 32 both structured in the form of one-way valves. In at least one preferred embodiment of the present invention, the first one-way valve structure 30 and the second one-way valve structure 32 are integrally or fixedly attached and cooperatively operational so as to regulate fluid flow from the exterior of the casing 12, into the pressure chamber 16 and therefrom into the inflation lumen 15 and into the retaining cuff associated with the endotracheal tube.

In operation, when in the compressed position of FIG. 2, the valve assembly 28 is effectively inoperable since there is no forced or intended fluid flow through the casing 12. However, a withdrawal or outward positioning of the plunger 20 into the extended position, as represented in FIGS. 1, 3 and 4, will result in the first one-way valve structure 30 opening thereby allowing air to be drawn into the interior 24 of the plunger 20 about the periphery of the first one-way valve structure 30, such as at 33. During the filling of the interior 24 of the plunger 20, the second one-way valve structure 32 will remain closed, thereby preventing fluid flow from the interior of the pressure chamber 16 into the interior 24 of the plunger 20. However, once the plunger 20 is forced inwardly into the casing 12 and toward and into the compressed position of FIG. 2, the inwardly directed force, indicated by directional arrow 35 in FIG. 3, will cause a closing of the first one-way valve structure 30 and a concurrent opening of the second one-way valve structure 32. As a result, the air or other fluid collected within the interior 24 of the plunger 20 will be forced through the second one-way valve structure 32 into the pressure chamber 16. Accordingly, it should be apparent that the first and second one-way valve structures 30 and 32 will automatically and alternatively be disposed in an opened/closed position as the plunger 20 is withdrawn out into its extended position and subsequently forced inwardly into its compressed position as represented in FIGS. 2-4.

Therefore, the air or other fluid forced into the pressure chamber 16 will pass into a delivery channel 40 having an entrance 42 communicating directly with the interior of the pressure chamber 16. An exit or delivery end of the channel 40 is designated as 44, wherein an end most channel segment 44' will deliver a forced fluid flow through the connecting assembly 17 directly to the connecting collar 80 of the hub 82, of the inflating lumen 15. The end channel segment 44' is passes through the connecting assembly 17 and is disposed in fluid communication with the connecting collar 80 through the receiving port 14' associated with the distal end 14 of the casing 12. As set forth above, the distal end 14 may be removably connected to the inflating lumen 15, as primarily represented in FIGS. 12-14, by an interconnection between the connecting assembly 17 and the connecting collar 80 and hub 82, as will be described in greater detail hereinafter with primary reference to FIGS. 12-15.

Therefore, it should be apparent that a forced fluid flow from the interior of the plunger 20 into the pressure chamber 16 will serve to deliver a predetermined quantity of air or other inflating fluid through the pressure chamber 16 and into and along the length of the channel 40. Such fluid flow will continue to pass through the exit end 44 and channel segment 44' of the channel 40 and exit from the casing 12 through the receiving port 14'. Therefore the pressure chamber 16 and the interior of the retaining or pressure cuff will normally be maintained in fluid communication with one another. As a result the "existing pressure" within the pressure chamber 16 will be the same as the pressure within the inflated retainer cuff, as long as the casing 12 is operatively connected to the inflating lumen 15.

While a preferred embodiment of the present invention comprises the pump assembly 18 structured as an integrated and/or permanent part of the casing 12, it is noted that the a removable pump assembly, having similar operative and structural characteristics such as, but not limited to, a removably connected syringe type assembly, can be operative with the to the casing 12 without departing from the spirit and scope of the present invention.

Figure 5:
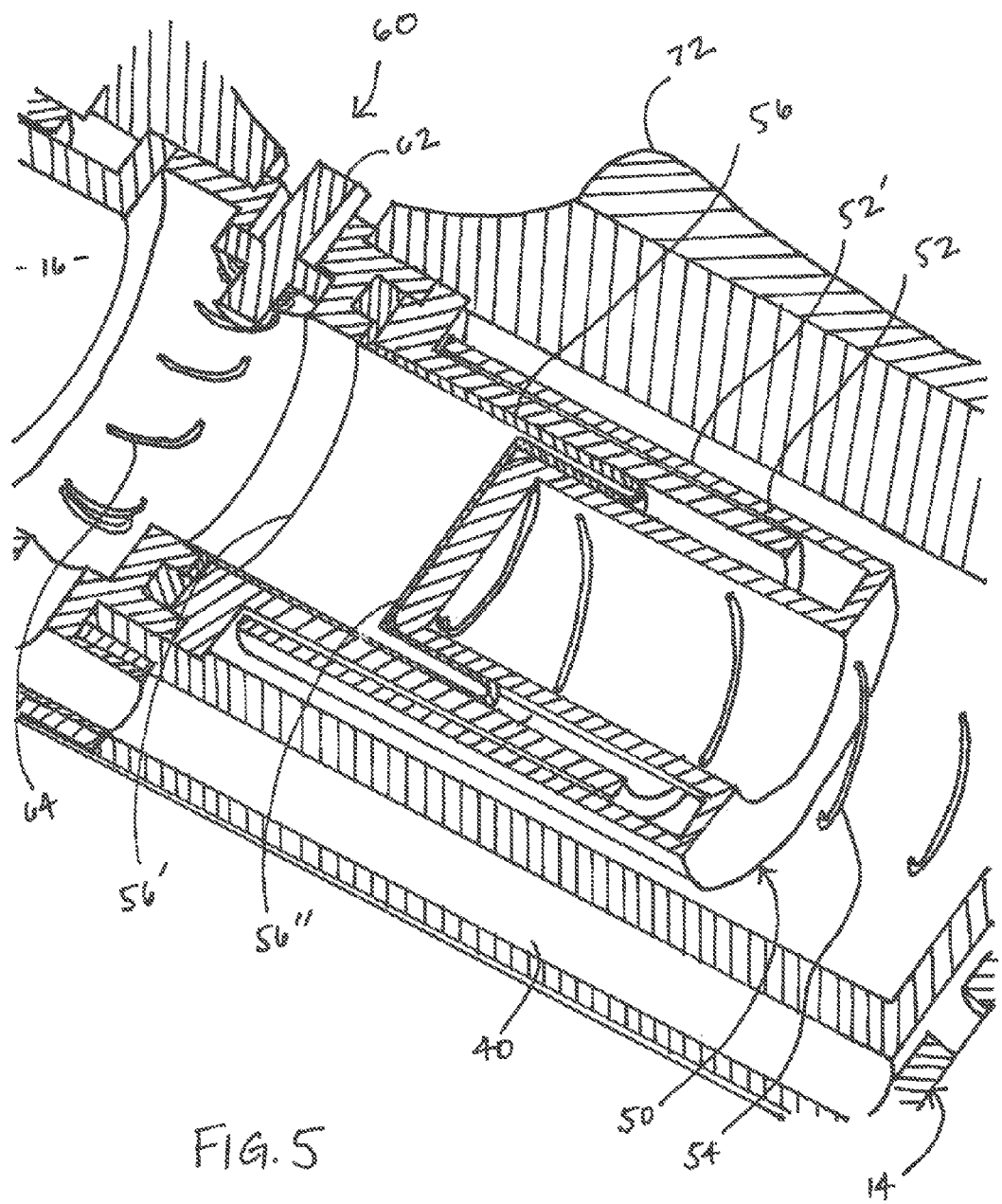
FIGS. 5-7 are detailed longitudinal sectional views of an indicator assembly of the embodiment of FIGS. 1-4, in successively different stages of operation.
Figure 6:
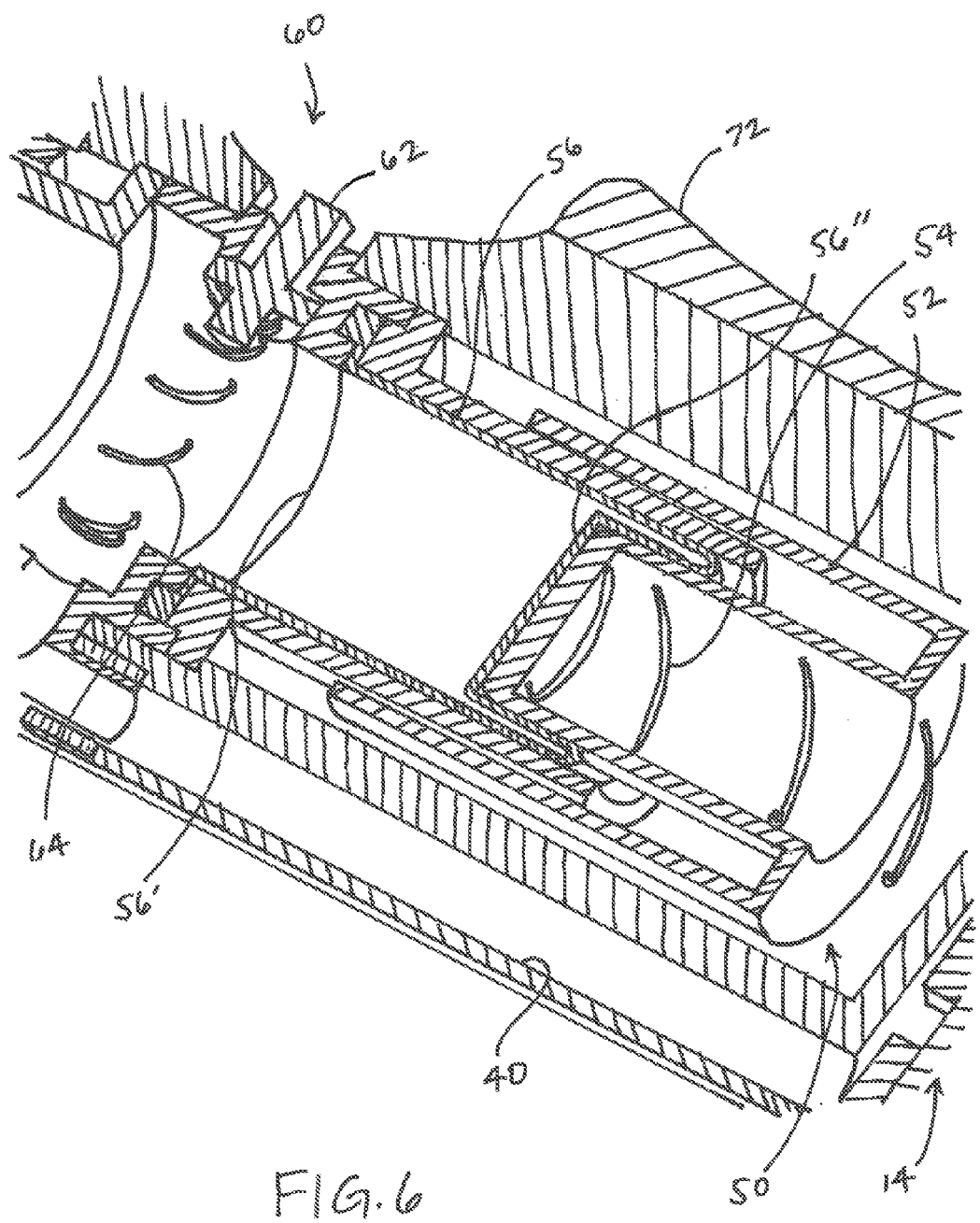
Figure 7:
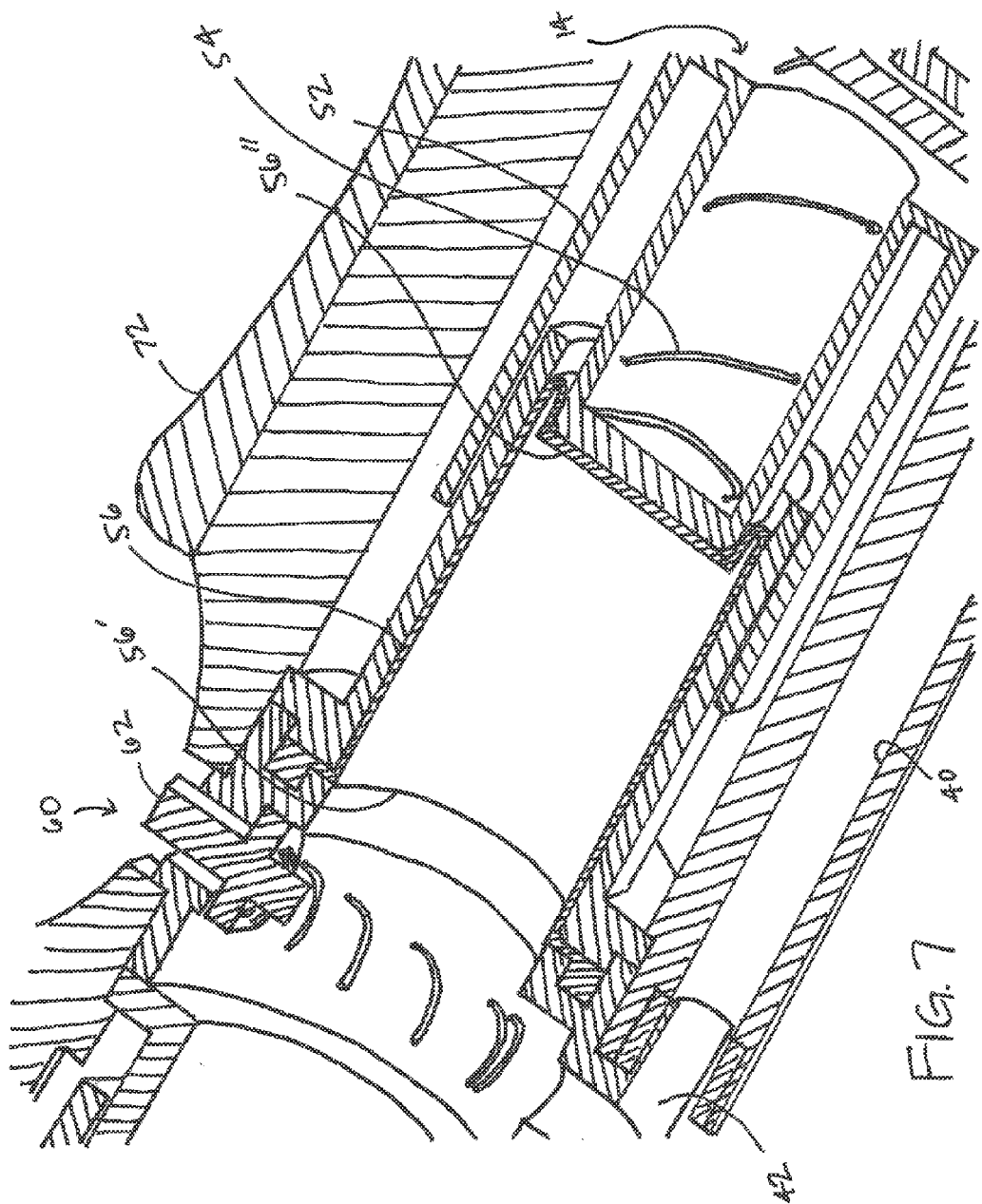

Another feature of at least one preferred embodiment of the present invention is the provision of an indicator assembly generally indicated as 50 represented in different stages of operation in FIGS. 5-7, dependent on the magnitude of the "existing pressure" within the pressure chamber 16 and accordingly, within the retaining cuff. More specifically, the indicator assembly 50 includes an indicator member 52 movably disposed on and more specifically within the casing 12 in direct fluid communication with the pressure chamber 16. Accordingly, any existing pressure within the pressure chamber 16 will be cause a force to be exerted on the indicator assembly 50 and more specifically on the indicator member 52. As also represented, the movement of the indicator member 52 is at least partially the result of it being biasingly mounted or disposed within the interior of the casing 12. Such a biased mounting or connection of the indicator member 52 is accomplished through the provision of a biasing member 54 preferably, but not necessarily, including at least one spring. As such, the biasing member 54 typically biases the indicator member 52 in a direction towards the pressure chamber 16 and against or in confronting relation with the bladder 56 defining an interconnecting member, which is associated with the with the indicator assembly 50, as explained in greater detail hereinafter. Accordingly, the biasing member 54 biases the indicator member 52 against the existing force present within the pressure chamber 16.

Therefore, as a result of the forces concurrently exerted on the indicator member 52 by the biasing member 54 and the existing pressure within the pressure chamber 16, the indicator member 52 is "variably positioned" within the interior of the casing. The biasing force exerted on the indicator member 52 by the biasing member 54 and may be predetermined and as such relatively constant or at least predictable. Accordingly, the movement of the indicator member 52 and its variable position within the casing 12 is directly dependent on the magnitude of the existing pressure within the pressure chamber 16 and the resulting variable force exerted on the indicator member 52. Additional structural and operative features of the indicator assembly 50 include the aforementioned interconnecting member in the form of the bladder 56, formed of a flexible material. The bladder 56 includes an open end 56' disposed and dimensioned to establish direct fluid communication with the interior of the pressure chamber 16. The opposite end or other appropriate portion as at 56" is connected to or is otherwise disposed in confronting, driving relation to a corresponding portion of the indicator member 52. Any existing pressure within the pressure chamber 16 will result in a proportional force being exerted on the flexible material bladder 56 and transferred to the indicator member 52 and against the biasing force exerted on the indicator member 52 by the biasing member 54. Therefore, the existing pressure within the pressure chamber 16 will exert a variable force on the bladder 56 and thereby on the indicator member 52 and against the biasing member 54, depending on the magnitude of this existing force.

With primary reference to FIGS. 5-7 and a comparison of the position of the indicator member 52 in these Figures, it is clearly demonstrated that the variable position of the indicator member 52 will be dependent on the force exerted on the bladder 56 and indicator member 52 based on the magnitude of the existing pressure within the pressure chamber 16 and the counteracting force exerted on the indicator member 52 by the biasing member 54.

More specifically, FIG. 5 represents one operative position of the indicator member 52, wherein a first, relatively smaller amount of force is exerted on the indicator member 52 due to a smaller magnitude of existing pressure within the pressure chamber 16. However this relatively smaller force is still adequate to at least partially overcome the biasing force exerted on the indicator member 52 by the biasing member 54. In contrast, the position of the indicator member 52 indicates that the magnitude of the existing pressure within the pressure chamber 16 has significantly increased and is proportionately greater than the biasing force exerted on the indicator member 52 by the biasing member 54 in that the indicator member 52 is forced more closely to the proximal end 14 and against the biasing member 54. Moreover, FIG. 7 represents an even greater increase in the force being exerted on the bladder 56 and indicator member 52, due to a significantly greater increase in the magnitude of the existing pressure within the pressure chamber 16. As a result, the position of the indicator 52 has again varied as it is forced even more closely to the proximal end 14 of the casing 12.

Accordingly, it is again emphasized that the existing pressure within the pressure chamber 16 will be substantially equivalent to the existing pressure within the retaining cuff associated with the endotracheal tube when it is inflated. This is due to the open line of fluid communication between the pressure chamber 16 and the interior of the retainer cuff once inflated and when the pump assembly 18 specifically including the plunger 20 is in its compressed position as represented in FIG. 2. Therefore, the variable position of the indicator member 52 within the casing 12 is indicative of the magnitude of pressure within the retaining cuff as well as the pressure chamber 16.

Additional features associated with the indicator assembly 50 preferably include the provision of indicating indicia 53 present on the exterior surface 52' of the indicator member 52. Further, the casing 12 includes a window or like structure 58 which facilitates a visual observation of the exterior surface 52' of the indicator member 52 as well as the indicating indicia disposed thereon. Such indicating indicia 53 may be in the form of a color coded segment or segments on the exterior surface 52' and/or any type of other appropriate markings which are disposed and structured to facilitate a clear visual indication of an adequate or proper pressure within the pressure chamber 16 and accordingly within the retaining cuff. By way of example only, a color coded portion may exist on the exterior surface 52' which will provide an individual, having visual access to the window 58, with a clear indication that at least the minimum or adequate amount of pressure exists within the retainer cuff. Such color coding may include a "red" surface area segment which will quickly inform an observer that the retainer cuff may be over inflated or include excess pressure on the interior thereof.

In addition, a magnifying lens or other magnifying structure may be included in or as part of the window 58, in order to further facilitate the visual observation of the indicating indicia 53 on the surface 52'. Yet additional embodiments of the present invention may include an LED or other appropriate digital readout, as well as an audible and/or visual warning, associated with the exterior of the casing 12, such as in the vicinity of the window 58, in the event of an over inflation condition of the cuff.

Figure 8:
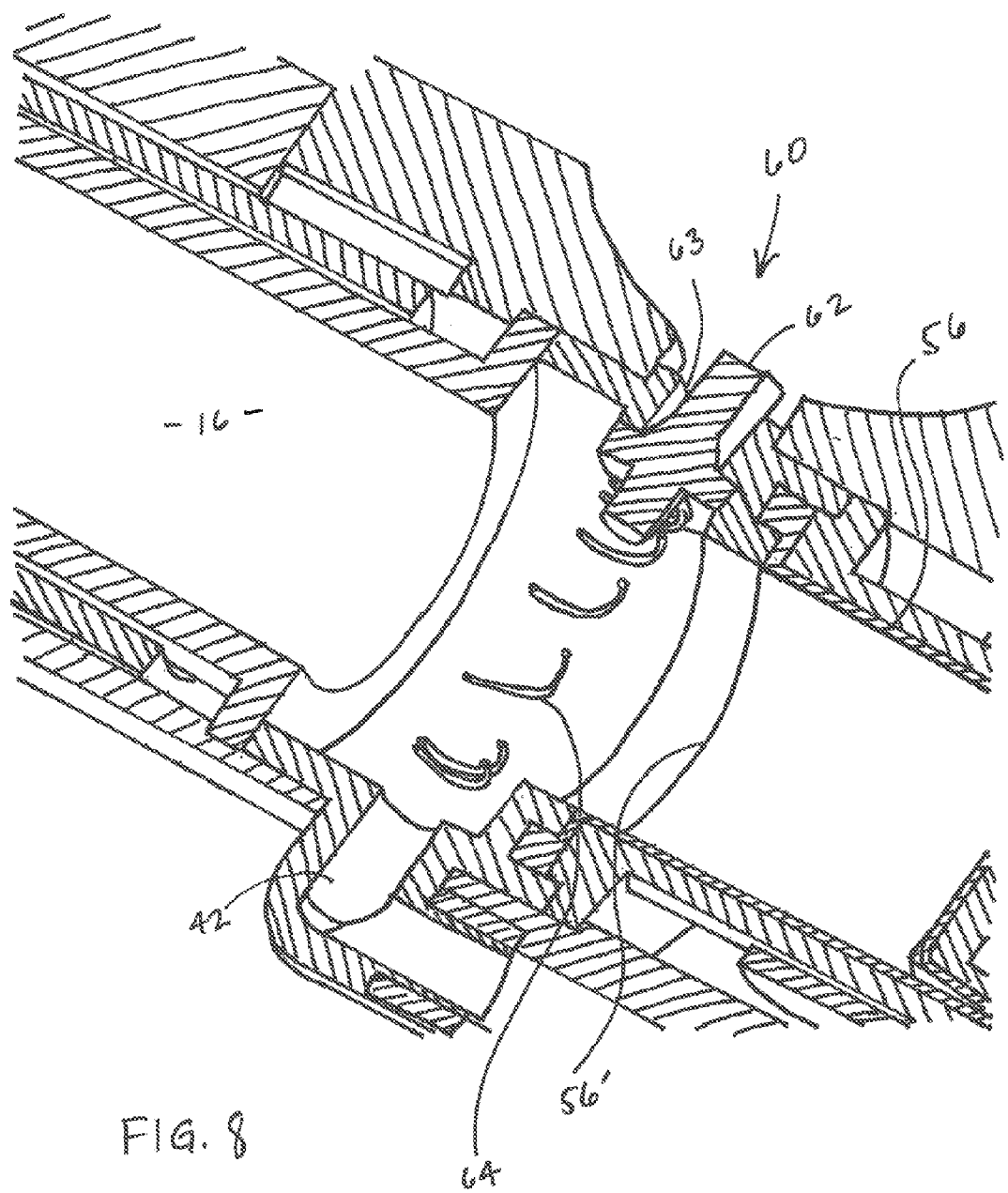
FIG. 8 is a detailed longitudinal sectional view in partial cutaway of a pressure relief assembly associated with the embodiment of FIGS. 1-7.
Figure 9:
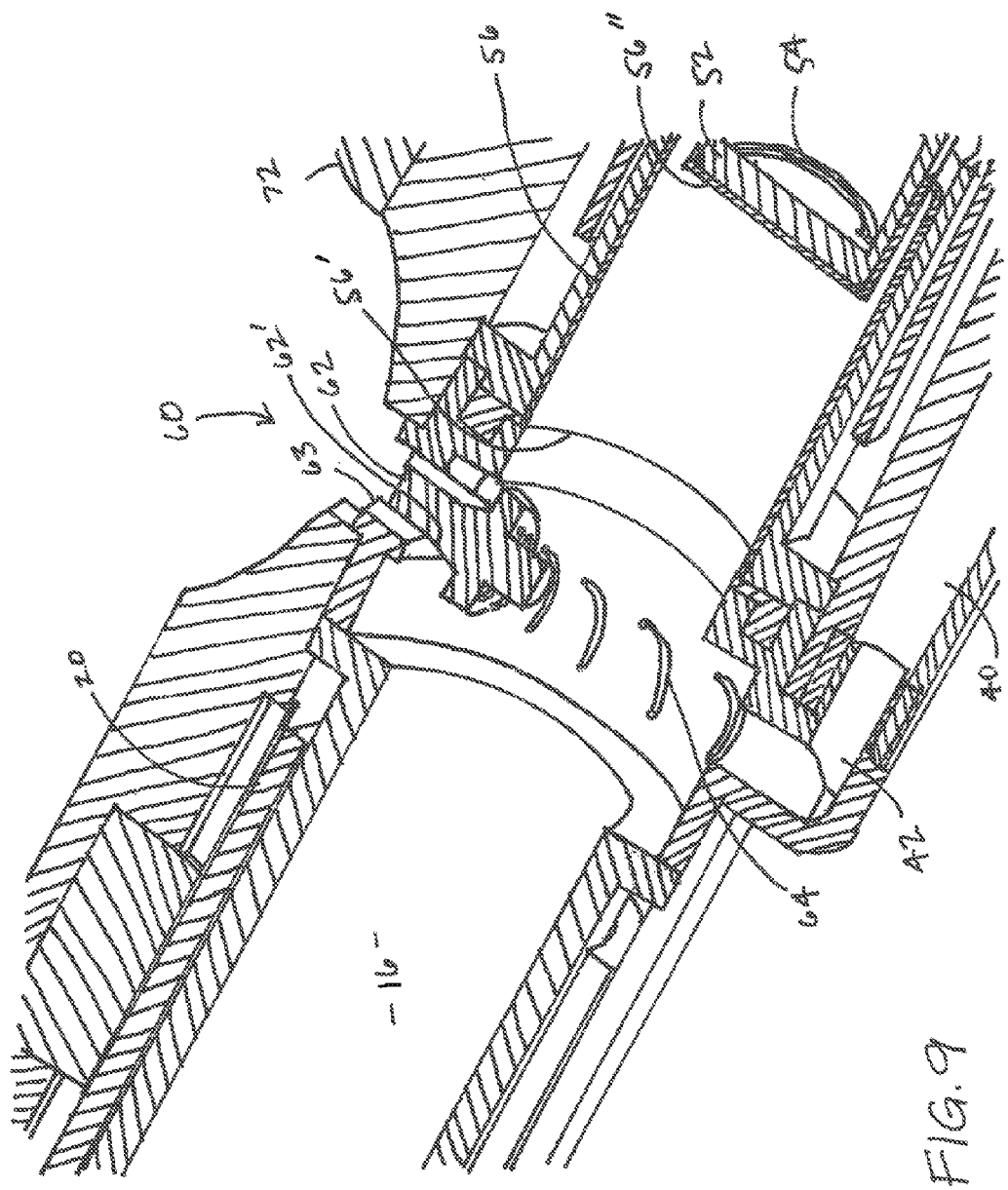
FIG. 9 is a detailed longitudinal sectional view of the embodiment of FIG. 8, wherein the pressure relief assembly is in an open, venting orientation.

In order to properly inflate, monitor and if necessary regulate the existing pressure within the pressure chamber 16 and accordingly within the retainer cuff, at least one preferred embodiment of the present invention includes a pressure relief assembly generally indicated as 60, as represented in FIGS. 8 and 9. The pressure relief assembly 60 includes a pressure relief valve 62, disposed in fluid sealing relation to the interior surfaces of the vent port or opening 63, wherein the valve 62 is accessible from the exterior of the casing 12 as represented. Further, the pressure relief valve 62 may be normally maintained in a closed position, as clearly represented in FIG. 8, due to the provision of a biasing member 64 in the form of one or more biasing springs. The biasing member 64 is disposed and structured to maintain the pressure relief valve 62 in a closed orientation unless an external, depressing pressure or force is applied thereto. As a result, in situations where the retainer cuff becomes over inflated or overly pressurized, the relief valve 62 may be depressed or otherwise manipulated to open the relief valve 62 thereby venting the existing pressure from within the pressure chamber 16. This in turn will cause a change in the force exerted on the indicator member 52 and result in a position change of the indicator member 52 in a direction toward the pressure chamber 16.

Such variable positioning of the indicator member 52 will be observable through the window 58 in the casing 12 as represented throughout the accompanying Figures. In addition, the structuring of the relief valve 62 may include a substantially tapered configuration, as at 62' in FIGS. 8 and 9, or other appropriate structural configuration to accomplish sealing engagement with the interior surfaces of the vent port or opening 63. This preferably tapered structure provides for a gradual bleeding or release of pressure from within the pressure chamber.

The provision of a pressure relief assembly 60 may be necessary and/or desirable to maintain an adequate control of the existing pressure within the pressure chamber 16. However, care must be taken to avoid or prevent any inadvertent venting of the existing pressure within the pressure chamber 16. Accordingly, at least one preferred embodiment of the present invention includes a restricting assembly generally indicated as 70. The restricting assembly 70 includes a finger manipulated slide structure 72 movable along the exterior of the casing 12, such as along the one or more rails 74.

Figure 10:
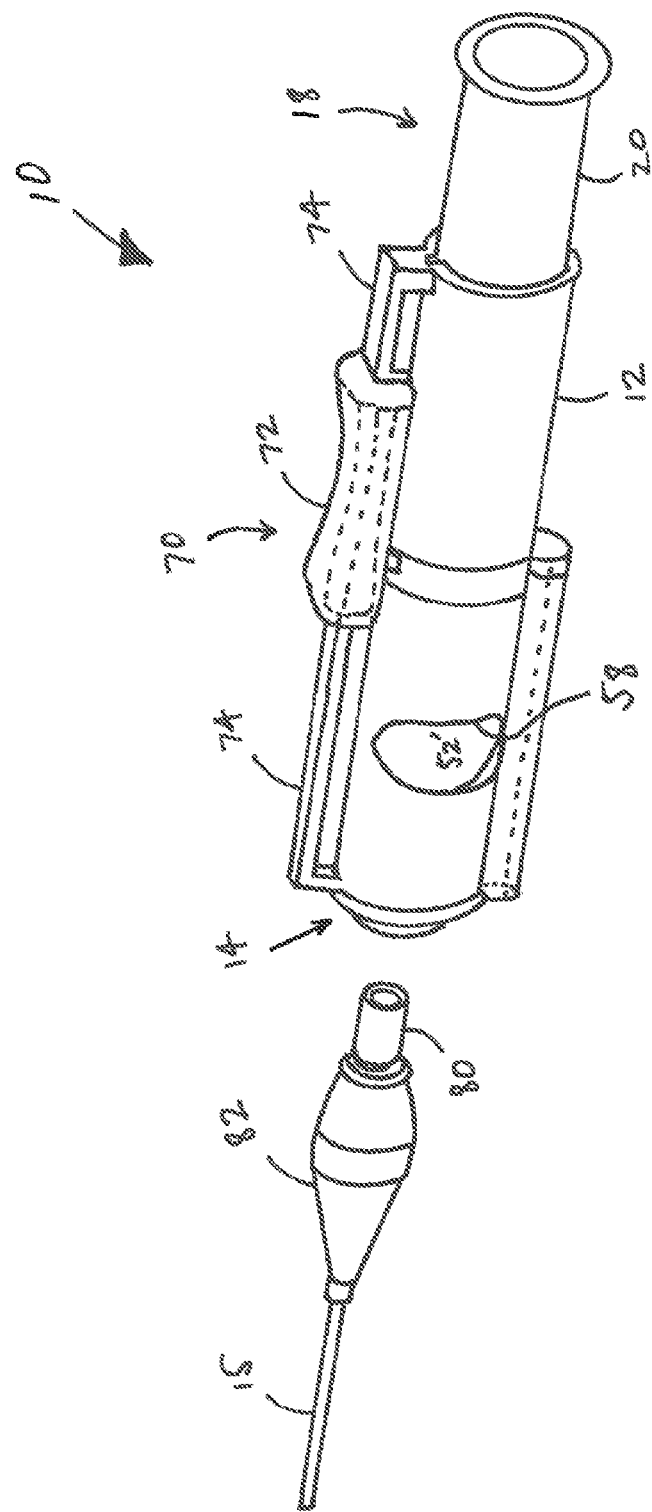
FIG. 10 is a perspective view in partially exploded form of the embodiment of FIGS. 1-9 wherein a restriction assembly is disposed in access restricting relation to the pressure relief assembly of the embodiment of FIGS. 8 and 9.
Figure 11:
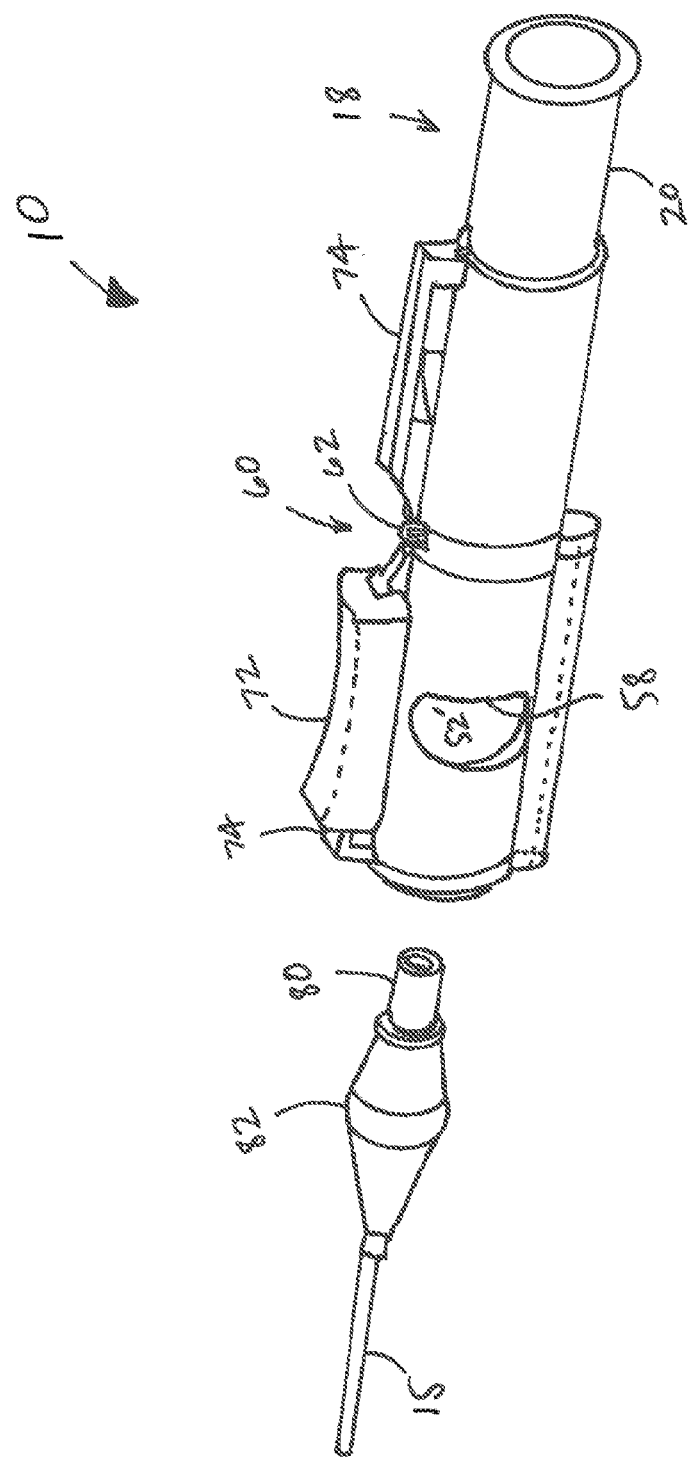
FIG. 11 is a perspective view in exploded form of the restriction assembly of the embodiment of FIG. 10 in a non-restricting position.

With primary reference to FIGS. 2, 3 and 11, the finger manipulated slide member 72 is disposed along an exterior portion of the casing 12 in spaced relation from the pressure relief assembly 60, thereby allowing clear access to the pressure relief valve 62. However, in contrast, FIGS. 1, 4 and 10 represent the position of the restricting slide member 72 in the position which restricts access to the pressure relief assembly 60 and in particular the pressure relief valve 62. As a result, the pressure relief valve 62 cannot be inadvertently or purposefully depressed thereby restricting an inadvertent venting of the pressure chamber 16 while the slide member 72 is in the restricting position.

As also noted in FIG. 4, when the slide member 72 is in the restricting position as indicated, a portion thereof as at 72' engages a lock or blocking structure 73 which may be selectively disposed into blocking or interruptive engagement with an end portion of the plunger 20, thereby preventing it from being forced inwardly into the aforementioned compressed position as represented in FIG. 2. As a result, the restricting assembly 70, specifically including the restricting slide member 72 is disposable on the casing 12 in movement restricting relation to the pump assembly 18 and in particular, the plunger 20. As also indicated in the embodiment of FIG. 4, the structure, dimension and configuration of the restricting member 72 may be such as to concurrently restrict movement of the plunger 20 as well as access to the pressure relief valve 62 of the pressure relief assembly 60.

Figure 12:
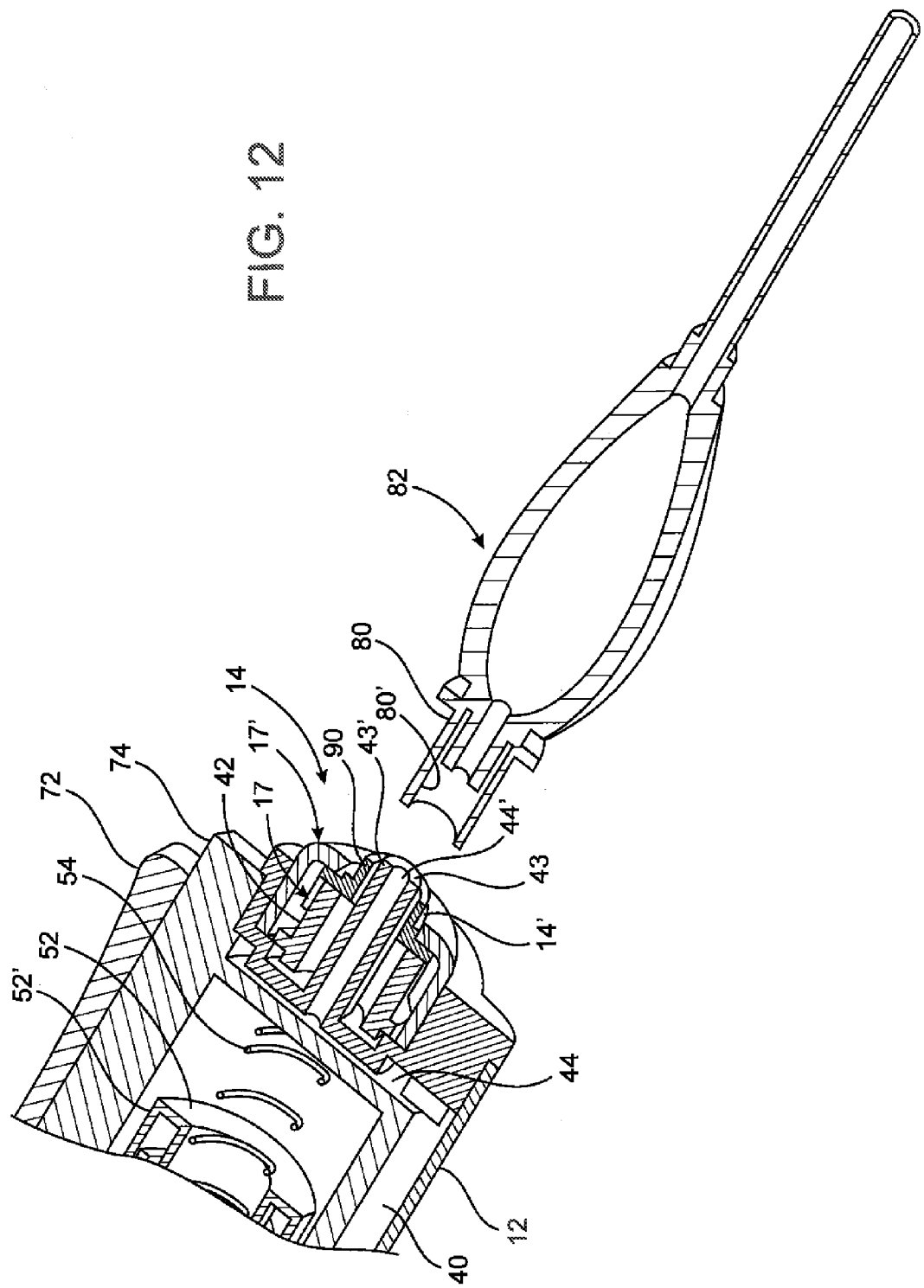
FIG. 12 is a detailed exploded view in partial cutaway and section of a connection assembly of the present invention structured to facilitate connection to an inflating lumen.
Figure 13:
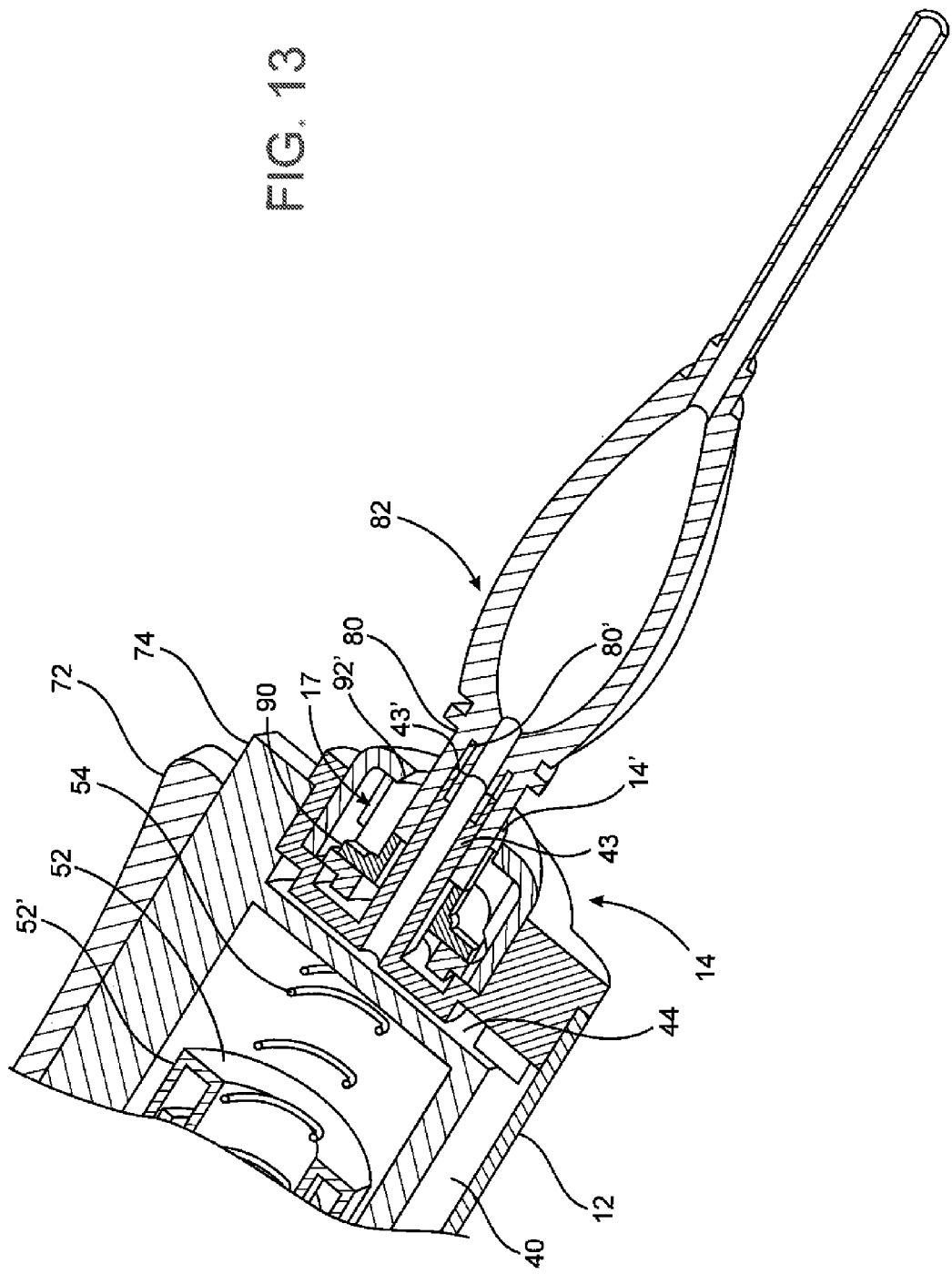
FIG. 13 is a detailed sectional view in partial cutaway of the embodiment of FIG. 12 wherein the connection assembly establishes a removable connection to the remainder of the flushing assembly of the present invention.
Figure 14:
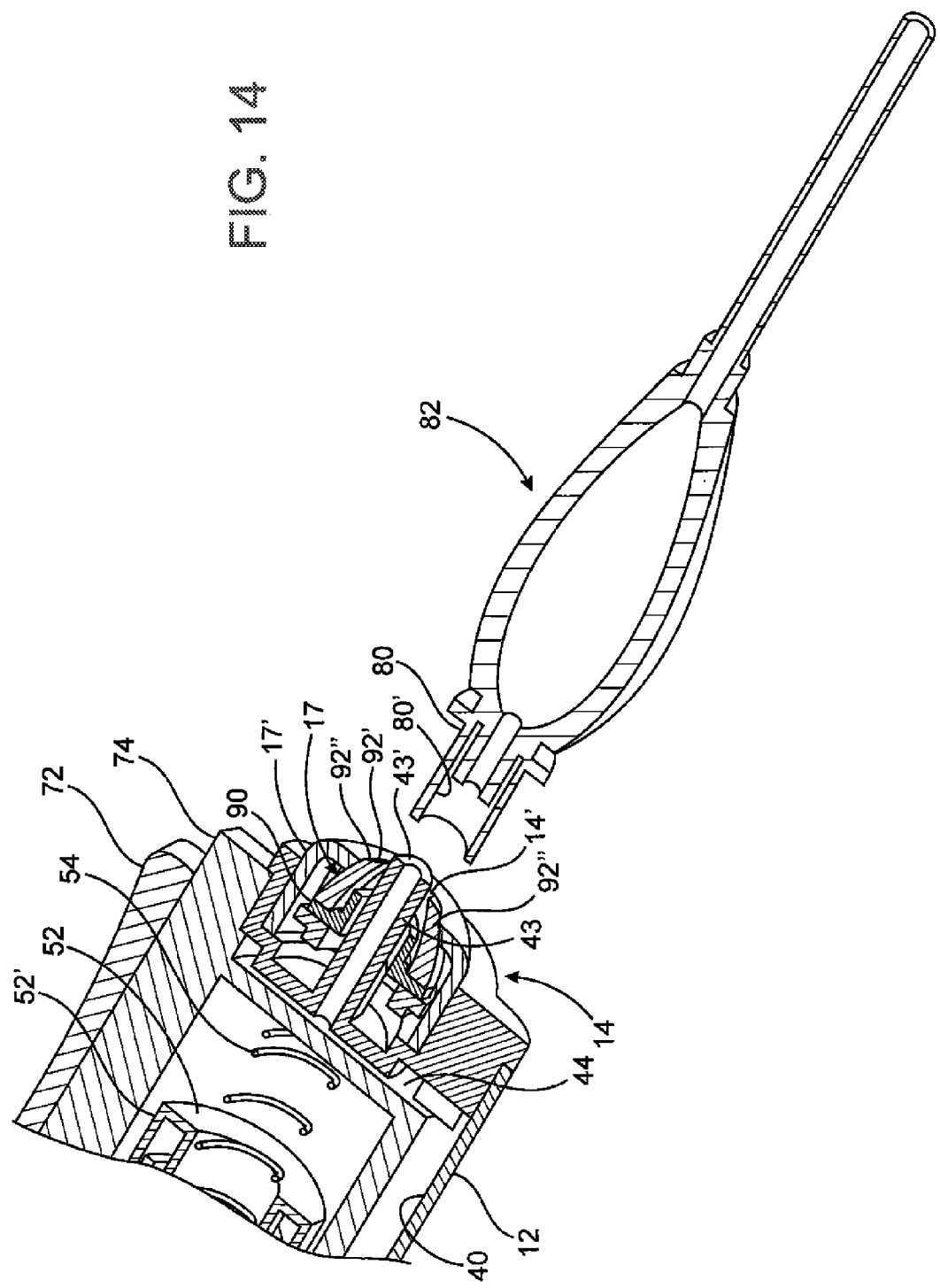
FIG. 14 is a exploded view in partial cutaway and section, wherein the inflating lumen has been removed from a remainder of the assembly of the present invention and wherein the connection assembly is structured to define a single-use device of the assembly of the present invention.

With primary reference to FIGS. 12-14, yet another preferred embodiment of the inflating and monitoring assembly 10 of the present invention comprises a connecting assembly 17. The structural and operative features of the connecting assembly 17 are such as to allow for only a single-use of the casing 12 and the various operative components associated therewith. More specifically, the connecting assembly 17 is directly associated with the distal end 14 of the casing 12 and is accessible through the receiving or connecting port 14'. As such, the receiving or connecting port 14' is dimensioned and configured to receive a connecting collar or like structure 80 associated with the hub 82 of the inflating lumen 15. The connecting collar 80 may be, but is not limited to, a luer type connector structured for connection to a cooperatively disposed and structured male luer type connector 43. The connecting collar 80 is dimensioned and configured to pass through the connecting port 14', as represented in FIG. 13. Once so positioned, a retaining member 90 associated with the connecting assembly 17 forced back into non-retaining relation with a gripping structure 92, as also represented in FIG. 13.

Although not specifically represented, the gripping structure 92 is associated with an appropriate biasing structure, which is disposed to bias the gripping structure 92 in a direction towards the connecting port 14'. Further, the retaining member 90, while being initially disposed adjacent to and/or extending outwardly from the port 14', is movable on or relative to the gripping structure 92 in direction away from the port 14', as the collar 80 passes through the port 14' and engages the retaining member 90. Accordingly, a comparison of FIGS. 12 and 13, clearly indicate that the retaining member 90 may be initially disposed, along with the other components of the connecting assembly 17, into a "connect position". However, upon entry of the collar 80 through the receiving port 14', the retaining member 90 is forced back away from the gripping structure 92, against the force exerted thereon by the aforementioned biasing structure. Advancement of the collar 80 through the port 14' and on to the male luer type fitting or like connector 43 accomplishes a frictional or other confronting engagement between the interior surface 80' of the hub 80, and an exterior preferably tapered surface 43' of the male connecting member 43. As a result, a fluid tight seal and connection is established between the interior surface 80' of the hub 80 and the exterior surface 43' of the nozzle or male luer type fitting.

With primary reference to FIGS. 13 and 14, a single use structuring of the connecting assembly 17 is demonstrated. More specifically, as the retaining member 90 is forced inwardly into the interior of the connecting assembly housing 17' it is effectively removed from a retaining relation to the outermost end 92' of the gripping member 92. Accordingly, as the casing 12 is disconnected from the inflating lumen 15, the collar 80 will be withdrawn from the interior of the connecting assembly housing 17', while the retaining member 90 will remain in the position represented in FIG. 14. However, due to the biasing force exerted on the gripping structure 92, as set forth above, the end 92' will be forced out of the connecting port 14' as indicated. As a result, the end 92' will assume a blocking or disconnect orientation due in part to a latching structure 92" formed on the outer surface of the end 92'. This latching structure 92" will overlap and effectively be latched onto the outer periphery of the connecting aperture 14' and thereby prevent the end 92' from passing back through the connecting aperture 14' into the interior of the connection assembly housing 17'.

As a result, it will be impossible or extremely difficult for the casing 12 to be reconnected to the hub 82 or collar 80 of the inflating lumen 15 once it has been disconnected there from, due at least in part to the fact that the collar 80 will not be able to be inserted back through the receiving or connecting port 14' into engagement with the male connector 43. It should be apparent therefore, that in the embodiment of FIGS. 12-14, the casing 12 can be easily and quickly removed from its operative connection to the inflating lumen 15 but once removed or disconnected cannot then be reconnected, as set forth above.

Figure 15:
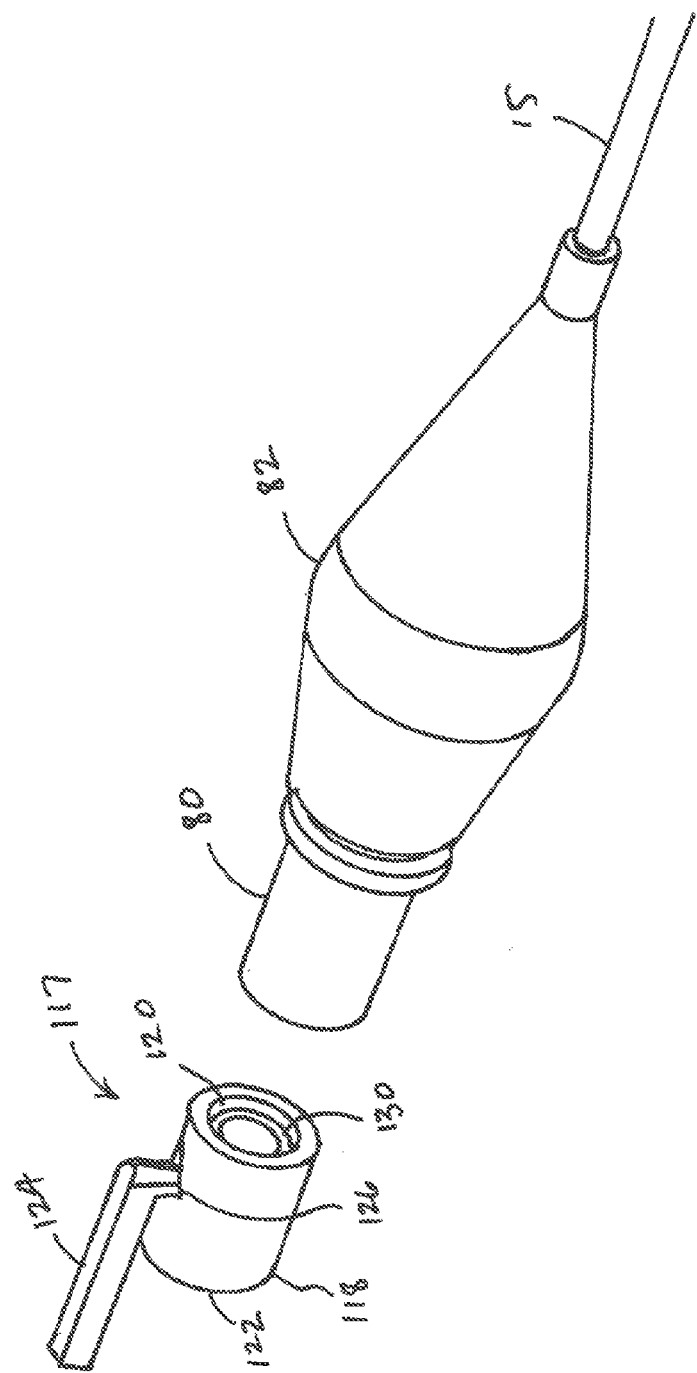
FIG. 15 is a perspective view in exploded form of the yet another embodiment of a connection assembly.

In addition to the above, at least one embodiment of the connection assembly 17 comprises the retaining member 90 and the gripping member 92 being of different, contrasting colors thereby clearly indicating whether the assembly 10 and the casing 12 is in the connect orientation and ready for us or in the disconnect orientation and has already been used. More specifically, as represented in FIG. 12 the casing 12 and the connection assembly 17 are in the connect orientation and have not been used in that the connection assembly 17 has not yet been connected to the collar 80 of the inflating lumen 15. As a result, the retaining member 90 is clearly visible through the connecting aperture 14'. In contrast, FIG. 15 represents the casing 12 and connection assembly 17 being in the disconnect orientation, wherein the collar 80 and connection assembly 17 having been disconnected from one another. Moreover, after use the gripping member 92 is clearly visible through the connecting aperture 14' and the retaining member 90 can no longer be seen. Accordingly, the production of the retaining member 90 and the gripping member in contrasting colors such as, but not limited to, green for the retaining member 90 and red for the gripping member 92, will provide a clear and readily observable indication as to whether or not the casing 12 has or has not been used.

As set forth above, the preferred embodiment Of FIGS. 12-15 is structured to accomplish a "single-use" inflation and monitoring assembly 10. However, structural modifications representing yet another embodiment of the present invention include the casing 12 being integrally, fixedly and/or at least partially permanently connected to the inflation lumen 15 such as by the interconnecting hub 82 and collar 80. In such an additional preferred embodiment, the structural and operative features of the connecting assembly 17 may be cooperatively modified along with the collar 80 and the hub 82 to accomplish the integration of the casing 12, collar 80 and hub 82 as a single unit.

With primary reference to FIGS. 15-17, yet another embodiment of the connection assembly is generally indicated as 117. While not directly disclosed, the connection assembly 117 is dimensioned and configured for insertion within the connection shell or housing 17' by being inserted through the connecting or receiving port 14'. Moreover, the connection assembly 117 includes a connection housing 118 having an open proximal end as at 120 and an open distal end as 122. When in a connect orientation, as represented in FIG. 15, member 124 is initially positioned in track segment 126. Upon engagement with the connecting collar 80 of the inflating lumen 15, the indicator member 124 will automatically be forced into the intermediate orientation represented in FIG. 16. As such the indicator member 124 will be forced out of the track segment 126 and be disposed as at a junction area 128 between the two track segments 126 and 129. Interaction between the connecting collar 80 and interior member 130 will cause the automatic disposition of the member 124 into the orientation or position represented in FIG. 16. Accordingly, the connection assembly 117 is designed to facilitate interconnection between the connecting collar 80 and end 120 of the connection housing 118 by being disposed in confronting engagement therewith or passing into the interior of the open end 120 into engaging relation with the interior member 130.

Structural features of the connection assembly 117 further provide for the removal or disconnection of the hub 82 from the connection assembly 117 as represented in FIG. 17. Accordingly, once a disconnection occurs between the connecting collar 80 the member 130, due to a biased connection and/or structure, will be forced outwardly through the opposite open end 122 concurrent to the movement or passage of the member 124 passing along the track segment 129 to an inner most end thereof, as also represented in FIG. 17. Therefore, the connection assembly 117, as represented in FIG. 17, at least partially defines a disconnect orientation or position of the connection assembly 117 in that the protrusion of the member 130 outwardly from the interior of the connection housing 118 will prevent reconnection of the connecting hub with or into interior of the housing 118. As a result, the connection assembly 117 is thereby structured to facilitate the casing 12 being structured as a "single-use" device due to the fact that the connection assembly 117 will not allow reconnection with the connecting collar 80 of the inflating lumen 15.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An assembly structured to inflate and to monitor pressure within a retaining cuff associated with an artificial airway tube, said assembly comprising:
    a casing including a pressure chamber disposed therein,
    a pump assembly movably connected to said casing and structured to force fluid flow to the retaining cuff through said pressure chamber,
    an indicator assembly disposed in fluid communication with said pressure chamber and including an indicator member,
    said indicator member variably positionable on said casing dependent on and indicative of existing pressure within said pressure chamber,
    said pressure chamber disposed in fluid communication with the retaining cuff, wherein said existing pressure within said pressure chamber is substantially equivalent to pressure within the retaining cuff,
    a pressure relief assembly mounted on said casing in fluid communication with said pressure chamber, said pressure relief assembly structured to selectively regulate existing pressure within said pressure chamber and the retaining cuff,
    wherein said pressure relief assembly comprises a relief valve operatively accessible from an exterior of said casing and disposed in regulating relation to fluid flow from said pressure chamber to the exterior of said casing, and
    a restricting assembly movably mounted on said casing and disposable in access restricting relation to said relief valve.

2. An assembly as recited in claim 1 wherein said pump assembly comprises a plunger movably connected to said casing and a valve assembly; said valve assembly disposed and structured to regulate fluid flow from said plunger to said pressure chamber.

3. An assembly as recited in claim 2 wherein said valve assembly comprises a first valve member and a second valve member, cooperatively disposed and structured to regulate fluid flow from an exterior of said casing into said pressure chamber, through an interior of said plunger.

4. An assembly as recited in claim 3 wherein said first and second valve members are alternately disposed in an open position and a close position to regulate fluid flow from an exterior of said casing into said pressure chamber, through said interior of said plunger.

5. An assembly as recited in claim 4 wherein said first and second valve members each comprise a one-way valve structure concurrently operable in interconnecting relation between said plunger interior and said pressure chamber.

6. An assembly as recited in claim 5 wherein said first and second valve members are integrally connected to one another to define a one piece construction.

7. An assembly as recited in claim 1 wherein said indicator assembly comprises a connector disposed in movably interconnecting relation between said indicator member and said pressure chamber.

8. An assembly as recited in claim 7 wherein said connector comprises a flexible material bladder disposed in fluid communication with said pressure chamber and in driving relation to said indicator member; said variable positioning of said indicator member being dependent on said existing pressure within said chamber, being exerted on said bladder.

9. An assembly as recited in claim 7 wherein said indicator member is biasingly mounted within said casing in normally opposing relation to said existing pressure within said pressure chamber.

10. An assembly as recited in claim 1 wherein said restricting assembly is movably disposed on said casing in movement restricting relation to said pump assembly.

11. An assembly as recited in claim 10 wherein said restricting assembly is structured for concurrent disposition in said restricting relations to said relief valve and said pump assembly.

12. An assembly as recited in claim 1 further comprising a restricting assembly movably mounted on said casing and disposable in operation restricting relation to said pressure relief assembly.

13. An assembly as recited in claim 1 further comprising a connection assembly disposed in interconnecting relation between said casing and an inflation lumen of the retaining cuff; said connection assembly disposable between a connect orientation and a disconnect orientation.

14. An assembly as recited in claim 13 wherein said connection assembly is structured to establish fluid flow between said casing and the retaining cuff when in said connect orientation.

15. An assembly as recited in claim 13 wherein said connection assembly is structured to establish disconnect of said casing from the inflation lumen and prevent reconnection therebetween.

* * * * *